United States Patent [19]

VandenBerg

[11] Patent Number: Plant 6,614

[45] Date of Patent: Feb. 21, 1989

[54] CHRYSANTHEMUM PLANT NAMED DARK TAN

[75] Inventor: Cornelis P. VandenBerg, Salinas, Calif.

[73] Assignee: Yoder Brothers, Inc., Barberton, Ohio

[21] Appl. No.: 94,718

[22] Filed: Sep. 9, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Dark Tan particularly characterized by its flat capitulum form; daisy capitulum type; greyed-orange ray floret color; diameter across face of capitulum of up to 6.0 cm at maturity when grown as a pinched spray pot mum; uniform eight week photoperiodic flowering response to short days; medium plant height when grown as a pinched pot mum; and semi-spreading branching pattern.

3 Drawing Sheets

The present invention comprises a new and distinct cultivar of Chrysanthemum, botanically known as *Chrysanthemum morifolium,* Ramat., and referred to by the cultivar name Dark Tan.

Dark Tan, identified as 79P62A18, is a product of a mutation induction program which had the objective of creating new Chrysanthemum cultivars that would expand the color range of an existing cultivar while retaining all other traits.

Dark Tan was discovered and selected by Cornelis P. VandenBerg on Sept. 7, 1984 in a controlled environment in Salinas, Calif. as one flowering plant within a flowering block established as rooted cuttings from stock plants which had been exposed as unrooted cuttings to an X-ray source of 1750 rads. The irradiated parent was the cultiver identified as Tan, disclosed in U.S. Plant Pat. No. 5,619.

The first act of asexual reproduction of Dark Tan was accomplished when vegetative cuttings were taken from the initial selection in November of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dark Tan are firmly fixed and are retained through successive generations of asexual reproduction.

Dark Tan has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dark Tan, which, in combination, distinguish this Chrysanthemum as a new and distinct cultivar:

1. Flat capitulum form.
2. Daisy capitulum type.
3. Greyed-orange ray floret color.
4. Diameter across face of capitulum up to 6.0 cm at maturity, when grown as a pinched spray pot mum.

5. Uniform eight week photoperiodic flowering response to short days.
6. Medium plant height requiring 0 to 7 long days after pinch prior to short days and 1 application of 2500 ppm B-9 SP to attain a flowered plant height of 25 to 35 cm for year-round flowerings when grown as a pinched pot mum.
7. Semi-spreading branching pattern.

The accompanying photographic drawings show typical inflorescence and leaf characteristics of Dark Tan, with the colors being as nearly true as possible with illustrations of this type. Sheet 1 is a color photograph of Dark Tan grown as a pinched spray pot mum. Sheet 2 is a black and white photograph of three views of the inflorescence of Dark Tan. Sheet 3 is a black and white photograph showing the upper and under sides of the leaves of Dark Tan at three stages of development (mature, intermediate and immature).

Of the commercial cultivars known to the inventor, the most similar in comparison to Dark Tan is the parent cultivar Tan. All traits of Dark Tan are similar to those of Tan, except the color of ray florets, which is significantly darker than Tan. Dark Tan has a better color retention under high light conditions than Tan.

In the following description, color references are made to the Royal Horticultural Society Colour Chart. The color values were determined on plant material grown as a pinched spray pot mum in Salinas, Calif. on June 2, 1987.

Classification:

*Botanical.—Chrysanthemum morifolium,* Ramat., cv. Dark Tan.

*Commercial.*—Daisy spray pot mum.

INFLORESCENCE

A. Capitulum:

*Form.*—Flat.

*Type.*—Daisy.

*Diameter across face.*—Up to 6.0 cm at maturity.

B. Corolla of ray florets:

*Color (general tonality from a distance of three meters).*—Greyed-orange.

*Color (upper surface).*—Closest to 169A.

*Color (under surface).*—169C, streaked with 21B.

*Shape.*—Flat, oblong.

C. Corolla of disc florets:

*Color (mature).*—14A to 14B.

*Color (immature).*—144B to 144C.

D. Reproductive organs:

*Androecium.*—Present on disc florets only; moderate pollen.

*Gynoecium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Semi-spreading.

B. Foliage:

*Color (upper surface).*—137A to 137B.

*Color (under surface).*—137B to 137C.

*Shape.*—Lobed and slightly serrated.

I claim:

1. A new and distinct Chrysanthemum plant named Dark Tan, as described and illustrated, and particularly characterized as to uniqueness by the combined characteristics of flat capitulum form; daisy capitulum type; greyed-orange ray floret color; diameter across face of capitulum of up to 6.0 cm at maturity when grown as a pinched spray pot mum; uniform eight week photoperiodic flowering response to short days; medium plant height when grown as a pinched pot mum; and semi-spreading branching pattern.

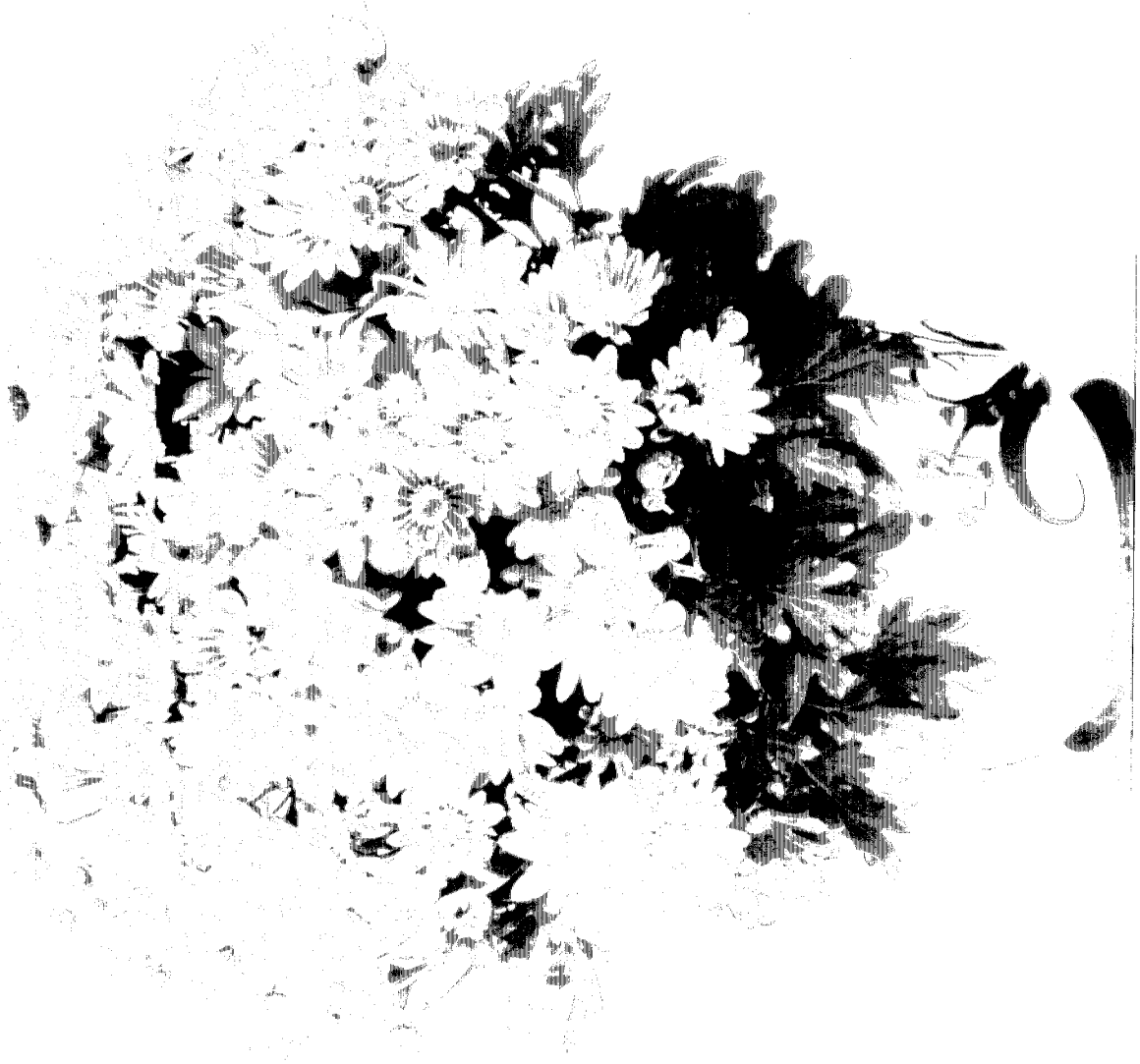

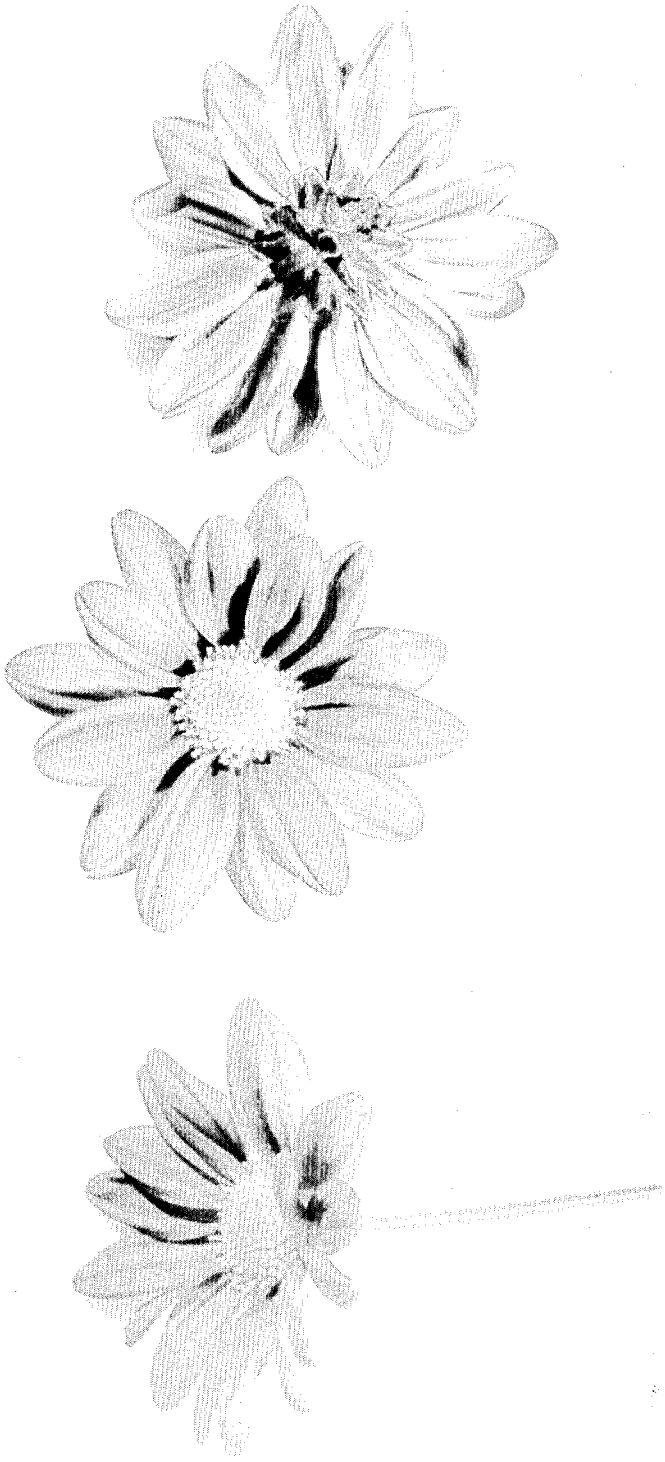

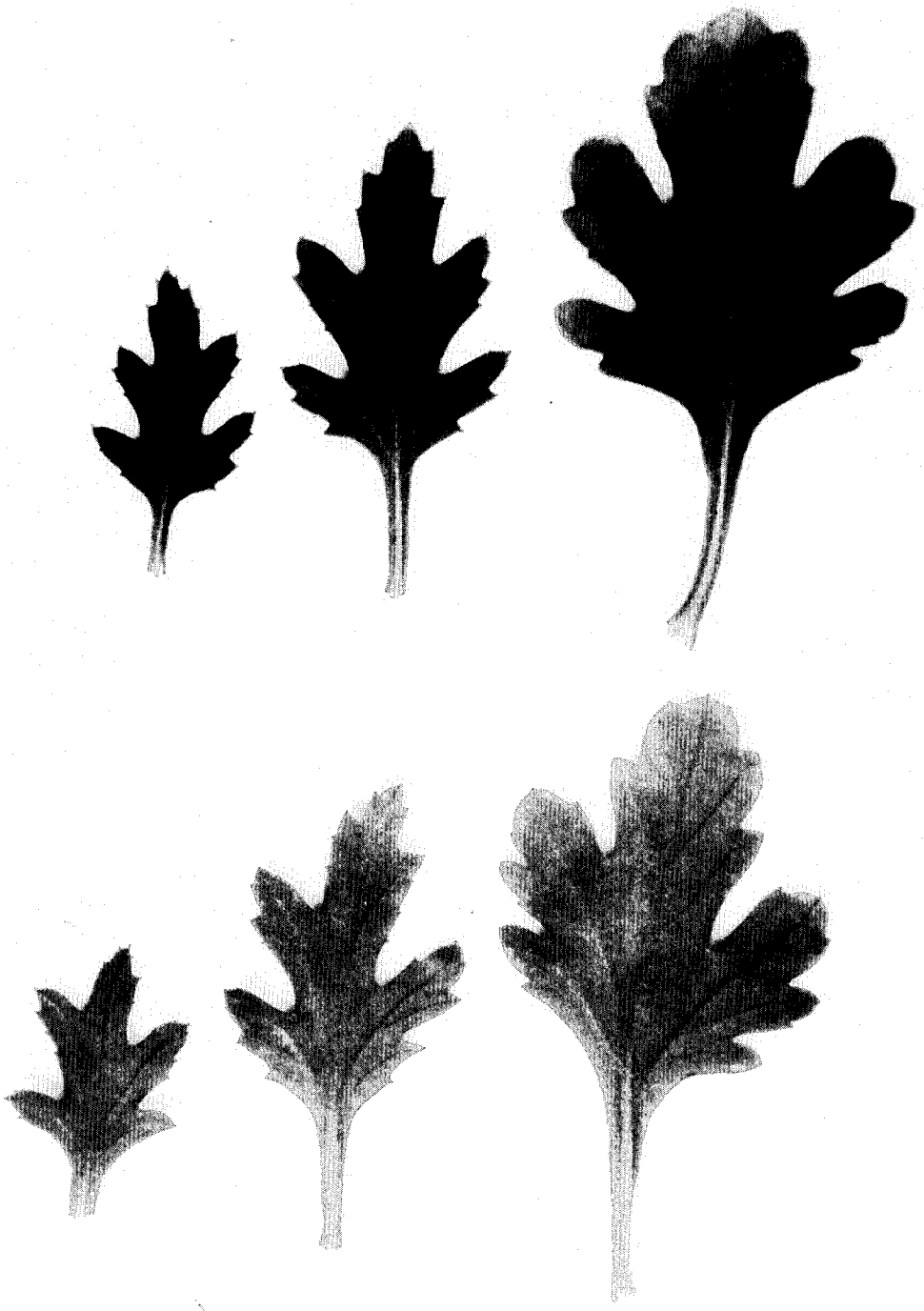

* * * * *